United States Patent
Wills

Patent Number: 5,524,645
Date of Patent: Jun. 11, 1996

[54] OBJECTIVE MEASUREMENT TOOL FOR EVALUATING MEDICAL THERAPY OUTCOME IN ACCORDANCE WITH QUANTIFIED PHYSICAL THERAPY DATA

[76] Inventor: Bruce R. Wills, 972 Whisperoak Dr., Melbourne, Fla. 32901

[21] Appl. No.: 407,961

[22] Filed: Mar. 22, 1995

[51] Int. Cl.$^6$ .................................. A61B 5/103
[52] U.S. Cl. ............... 128/898; 128/774; 128/782
[58] Field of Search ............... 128/898, 774, 128/782

[56] References Cited

U.S. PATENT DOCUMENTS

| | | | |
|---|---|---|---|
| 5,078,152 | 1/1992 | Bond et al. | 128/774 |
| 5,373,858 | 12/1994 | Rose et al. | 128/782 |

*Primary Examiner*—Angela D. Sykes
*Assistant Examiner*—Stephan Huang
*Attorney, Agent, or Firm*—Charles E. Wands

[57] ABSTRACT

A medical condition quantification and dysfunction-reduction therapy evaluation process enables a health care service provider to monitor the improvement of a patient's condition, as well as the efficiency of the rehabilitation process employed to achieve a patient improvement objective. Based upon initial patient examination data, one or more sets of parameters associated with respective body regions, for which dysfunction-reducing therapy is to be carried out, are provided. For each parameter, a data value is generated. The magnitude of the data value is based upon the condition of the body region associated with the parameter. All of the data values of the parameters of a body region are combined, to quantify the overall condition or dysfunction of the body region. Periodically, during the course of the patient therapy program, the physical condition of the body region being treated is re-examined. Based upon each re-examination, the numerical data value of each parameter is updated to reflect the current condition of body region, and the updated values are combined to thereby quantify the current dysfunction of the body region being treated. By graphically recording both the original quantification of the dysfunction and the iteratively updated quantification results of the therapy session, the progress of the patient therapy program in reducing dysfunction of the body region can be readily tracked, so as to enable the health care service provider to monitor whether the therapy is reducing the dysfunction, and how efficiently it is doing so.

32 Claims, 5 Drawing Sheets

| Cervical Spine / Upper Quarter / Thoracic Spine | Shoulder | Elbow / Wrist | Lumbar Spine / Lower Quarter / Hip | Knee | Ankle / Foot |
|---|---|---|---|---|---|
| Chart | Chart | Chart | Chart | Chart | Chart |
| ICD-9 | ICD-9 | ICD-9 | ICD-9 | ICD-9 | ICD-9 |
| Date | Date | Date | Date | Date | Date |
| 6  Gait | Gait | Gait | Gait | Gait | Gait |
| 12 AROM | AROM | AROM | AROM | AROM | AROM |
| 12 PROM | PROM | PROM | PROM | PROM | PROM |
| 12 Strength | Strength | Strength | Strength | Strength | Strength |
| 10 Palpation Pain | Palpation Pain | Palpation Pain | Palpation Pain | Palpation Pain | Palpation Pain |
| 10 Muscle Tone | Muscle Tone | Muscle Tone | Muscle Tone | Muscle Tone | Muscle Tone |
| 10 Swelling | Swelling | Swelling | Swelling | Swelling | Swelling |
| 10 Erythema | Erythema | Erythema | Erythema | Erythema | Erythema |
| 10 Effusion | Effusion | Effusion | Effusion | Effusion | Effusion |
| 10 Ecchymosis | Ecchymosis | Ecchymosis | Ecchymosis | Ecchymosis | Ecchymosis |
| 10 Edema | Edema | Edema | Edema | Edema | Edema |
| 10 Jt Mobility  122 | Jt Mobility | Jt Mobility | Jt Mobility | Jt. Mobility | Jt Mobility |
| 6 Alar Ligament Integrity | Yeargasons | Varus Stress | Hip Scour | Varus Stress | Anterior Drawer |
| 6 Vertebral Artery Test | Drop Arm | Valgus Stress | Post SI Compression | Valgus Stress | Calcaneal/Talar Tilt |
| 6 Vertebral Compression | Impingement | Tinels | Post SI Distraction | Ant. Drawer | Tibia/Fibula |
| 6 Vertebral Distraction | Apprehension | Phalens | SLR/Lesque | Post Drawer | Metatarsal Load |
| 6 Adsons | | Finkelstein | Hamstring Flexibility | Lachmans | Heel Pound |
| 6 Phalens | | | Abductor Flexibility | Mcmurrays | |
| 6 Hyperabduction | | | Hip External Rot. Flex | Patellar Compression | |
| 6 Tinels | | | Pelvic/Diaphram | Patellar Grind | |
| 6 Yergasons | | | Fabere | Apprehension | |
| 6 Drop Arm | | | Heel Pound | Apleys Grind | |
| 6 Impingement | | | Forward Bend March | Apleys Distraction | |
| 6 Apprehension | | | Long Sit Seated Forward Bend | Obers | |
| 194 | 146 | 152 | 310 | 194 | 152 |
| Total Score Vailable | Total Score Avail | Total Score Avl. | Total Score Available | Total Score Avail. | Total Score Avail. |
| Total Score Achieved | Total Score Achv | Total Score Achv | Total Score Achieved | Total Score Achiv | Total Score Achiv. |
| Total Treatments | Total Treatments | Total Treatments | Total Treatments | Total Treatments | Total Treatments |

| Cervical Spine<br>Upper Quarter<br>Thoracic Spine | Shoulder | Elbow<br>Wrist | Lumbar Spine<br>Lower Quarter<br>Hip | Knee | Ankle<br>Foot |
|---|---|---|---|---|---|
| Chart<br>ICD-9<br>Date | Chart<br>ICD-9<br>Date | Chart<br>ICD-9<br>Date | Chart<br>ICD-9<br>Date | Chart<br>ICD-9<br>Date | Chart<br>ICD-9<br>Date |
| 6 Gait<br>12 AROM<br>12 PROM<br>12 Strength<br>10 Palpation Pain<br>10 Muscle Tone<br>10 Swelling<br>10 Erythema<br>10 Effusion<br>10 Ecchymosis<br>10 Edema<br>10 Jt Mobility 122 | Gait<br>AROM<br>PROM<br>Strength<br>Palpation Pain<br>Muscle Tone<br>Swelling<br>Erythema<br>Effusion<br>Ecchymosis<br>Edema<br>Jt Mobility | Gait<br>AROM<br>PROM<br>Strength<br>Palpation Pain<br>Muscle Tone<br>Swelling<br>Erythema<br>Effusion<br>Ecchymosis<br>Edema<br>Jt Mobility | Gait<br>AROM<br>PROM<br>Strength<br>Palpation Pain<br>Muscle Tone<br>Swelling<br>Erythema<br>Effusion<br>Ecchymosis<br>Edema<br>Jt Mobility | Gait<br>AROM<br>PROM<br>Strength<br>Palpation Pain<br>Muscle Tone<br>Swelling<br>Erythema<br>Effusion<br>Ecchymosis<br>Edema<br>Jt Mobility | Gait<br>AROM<br>PROM<br>Strength<br>Palpation Pain<br>Muscle Tone<br>Swelling<br>Erythema<br>Effusion<br>Ecchymosis<br>Edema<br>Jt Mobility |
| 6 Alar Ligament Integrity<br>6 Vertebral Artery Test<br>6 Vertebral Compression<br>6 Vertebral Distraction<br>6 Adsons<br>6 Phalens<br>6 Hyperabduction<br>6 Tinels<br>6 Yergasons<br>6 Drop Arm<br>6 Impingement<br>6 Apprehension | Yeargasons<br>Drop Arm<br>Impingement<br>Apprehension | Varus Stress<br>Valgus Stress<br>Tinels<br>Phalens<br>Finkelstein | Hip Scour<br>Post SI Compression<br>Post SI Distraction<br>SLR/Lesque<br>Hamstring Flexibility<br>Abductor Flexibility<br>Hip External Rot. Flex<br>Pelvic/Diaphram<br>Fabere<br>Heel Pound<br>Forward Bend<br>March<br>Long Sit<br>Seated Forward Bend | Varus Stress<br>Valgus Stress<br>Ant. Drawer<br>Post Drawer<br>Lachmans<br>Mcmurrays<br>Patellar Compression<br>Patellar Grind<br>Apprehension<br>Apleys Grind<br>Apleys Distraction<br>Obers | Anterior Drawer<br>Calcaneal/Talar Tilt<br>Tibia/Fibula<br>Metatarsal Load<br>Heel Pound |
| 194<br>Total Score Vailable<br>Total Score Achieved<br>Total Treatments | 146<br>Total Score Avail<br>Total Score Achv<br>Total Treatments | 152<br>Total Score Avl.<br>Total Score Achv<br>Total Treatments | 310<br>Total Score Available<br>Total Score Achieved<br>Total Treatments | 194<br>Total Score Avail.<br>Total Score Achiv<br>Total Treatments | 152<br>Total Score Avail.<br>Total Score Achiv.<br>Total Treatments |

FIGURE 4

SCORING

| | | | | | |
|---|---|---|---|---|---|
| GAIT | WNL<br>6 | PROTECTED/GUARDED/ANTALGIC<br>4 | ASSISTIVE DEVICE<br>2 | PATHOLOGICAL<br>0 | DEFERRED<br>D |
| GROSS AROM | WNL<br>12 | FULL PAINFULL 10 9 8 7 6 5 4 3 2 1 0 % MOVEMENT | | | DEFERRED<br>D |
| PASSIVE ROM | WNL<br>12 | FULL PAINFULL 10 9 8 7 6 5 4 3 2 1 0 % MOVEMENT | | | DEFERRED<br>D |
| STRENGTH | | STRONG/PAINLESS(GRADE 5 NORMAL100%)<br>12 | STRONG/PAINFULL(Gd. 4, GOOD 80%)<br>9 | WEAK/PAINFULL (GRADE 3 fair 50%)<br>7 |     6 |
| DEFERRED | | WEAK/PAINLESS(GRADE 2 POOR 25%)<br>3 | GRADE 1 TRACE 10%<br>1 | ALL MOVEMENT PAINFULL(GRADE 0 0%)<br>0 | D |
| PALPATION PAIN | WNL<br>10 | LOCALIZED<br>7 5 3<br>MIN/MOD/EXT | RADIATING / EVERYTHING PAINFUL<br>0 | | DEFERRED<br>D |
| TISSUE | WNL<br>10 | INCREASED MUSCLE TONE<br>7 5 3<br>MIN/MOD/EXT | PATHOLOGICAL (HYPERTONICITY / HYPOTONICITY)<br>0 | | DEFERRED<br>D |
| | WNL<br>10 | SWELLING<br>7 5 3<br>MIN/MOD/EXT | PATHOLOGICAL<br>0 | | DEFERRED<br>D |
| | WNL<br>10 | ERYTHEMA<br>7 5 3<br>MIN/MOD/EXT | PATHOLOGICAL<br>0 | | DEFERRED<br>D |
| | WNL<br>10 | EFFUSION<br>7 5 3<br>MIN/MOD/EXT | PATHOLOGICAL<br>0 | | DEFERRED<br>D |
| | WNL<br>10 | ECCHYMOSIS<br>7 5 3<br>MIN/MOD/EXT | PATHOLOGICAL<br>0 | | DEFERRED<br>D |
| | WNL<br>10 | EDEMA<br>7 5 3<br>MIN/MOD/EXT | PATHOLOGICAL<br>0 | | DEFERRED<br>D |
| JOINT MOBILITY | WNL<br>10 | SLIGHT RESTRICTION W/O PAIN<br>SLIGHT INSTABILITY W/O PAIN<br>8 | SLIGHT RESTRICTION W/ PAIN<br>SLIGHT INSTABILITY W/ PAIN<br>6 | | |
| | | CONSIDERABLE RESTRICTION W/O PAIN<br>CONSIDERABLE INSTABILITY W/O PAIN<br>4 | CONSIDERABLE RESTRICTION W/ PAIN<br>CONSIDERABLE INSTABILITY W/ PAIN<br>2 | | |
| | | ANKYLOSIS/UNSTABLE<br>0 | DEFERRED<br>D | | |

SPECIAL TESTS

| | | | | | |
|---|---|---|---|---|---|
| LIGAMENTOUS LAXITY | WNL<br>6 | GRADE I<br>4 | GRADE II<br>2 | GRADE III<br>0 | DEFFERED<br>D |

1.
2.
3.
4.
5.
6.

| | NEGATIVE<br>6 | EQUIVOCAL<br>3 | POSITIVE (UNABLE TO ACHIEVE TEST POSITION)<br>0 | DEFFERED<br>D |
|---|---|---|---|---|

OBJECTIVE MEASUREMENT TOOL FOR EVALUATING MEDICAL THERAPY OUTCOME IN ACCORDANCE WITH QUANTIFIED PHYSICAL THERAPY DATA

FIELD OF THE INVENTION

The present invention relates in general to the evaluation of the progress of a patient therapy program, such as an orthopaedic therapy program for a patient's dysfunction, and is particularly directed to a mechanism for quantifying a patient's condition and any improvement of that condition, as well as the efficiency of the rehabilitation process employed to achieve a patient improvement objective.

BACKGROUND OF THE INVENTION

Due to the continued escalation of medical care costs, growth of managed health care, and the health care reform movement in general, there is increased pressure on health care service providers to establish cost containment programs. Unfortunately, there is no currently available medical diagnostic apparatus or methodology, which allows for objective quantification of an individual's orthopaedic movement function and/or physical therapy dysfunction, as it relates to various body regions, including cervical spine, thoracic spine, lumbar spine, shoulder, elbow, wrist, hip, knee, ankle, and foot. There is also no available mechanism that is capable of quantifying the severity of dysfunction of the various body regions of a patient as a result of a physical therapy initial evaluation; nor is there any routine available that allows for the objective measurement of the patient management process to include progression, improvement, and objective measurement of the efficiency of the overall physical therapy services (patient improvement divided by the number of treatment visits and cost).

Further, there is no mechanism by which physical therapy intervention and treatment outcomes can be objectively measured and numerically classified, so as to allow for comparative analysis regarding discharge, percent improvement, number of visits, and efficiency. There is also no procedure which objectively and numerically charts a patient's management process to include progress and improvement plateau, oscillation, or decline. There is no available scheme which provides for comparative data of a patient's initial evaluation, discharge, improvement, treatment visit number, and efficiency based upon body region or specific ICD-9-CM codes. (The commonly used notation "ICD-9-CM" corresponds to the International Classification of Diseases, 9th Revision, Clinical Modification, and refers to a coding system based upon and compatible with the original version of the ICD-9 coding system provided by the World Health Organization. The ICD-9-CM coding system is used in North America, and it is a classification of diseases, injuries, impairments, symptom, medical procedures, and causes of death, These codes are listed in detail in a publication of the Commission on Professional and Hospital Activities, Ann Arbor, Mich., entitled "ICD-9-CM," Jan. 1, 1979.)

There is also no method available which allows for comparisons between different physical therapist efficiencies and improvements of specific ICD-9 codes, body region, and overall treatment results of a general physical therapy patient, or which allows for objective measurement and comparisons of physical therapy corporations, efficiency of physical therapy services, and results obtained from specific body regions, or specific ICD-9 codes. In fact, there is no objective outcome measurement tool which utilizes physical therapy documentation.

This inability of the treating health care service provider to quantify the extent of dysfunction and recovery therefrom causes uncertainty in the treatment protocol, as well as the psychological uneasiness in the patient being treated. This inability to quantify dysfunction has also unfortunately frequently been the source of fraudulent medical claims against insurance carriers and patients, resulting in arbitrary fee and reimbursement capitations and treatment visit restrictions, which are only implemented from a financial perspective and have no bearing upon the patient status.

Such inability of conventional therapy procedures to quantify patient dysfunction has also resulted in a lack of cooperation and collaboration among health care service providers as to what treatment protocols are the most effective and efficient, and therefore has hindered the growth and expanse of medical knowledge.

Although there have been various attempts to provide quantitative measures of the severity of a patient's dysfunction, such prior methods have focused upon a specific body area and diagnosis, most notably the lumbar spine or knee, and are also dependent upon a specific treatment intervention. The outcome measures are not comparative with other providers or to other patient population with the same diagnosis.

Other methodologies require specialized certification or an MD degree and costly equipment, impairment ratings, or functional capacity assessments. These also have no correlation with the initial physical therapy evaluation, subsequent treatment intervention, and patient improvement. None provide for comparative statistics for diagnosis, body region, therapist, and corporation; and none pertain to the routine physical therapy evaluation, treatment and discharge, or patient management process. Still others have attempted to draw conclusions from data correlated and derived from the application of subjective patient reported pain ratings and patient satisfaction questionnaires.

SUMMARY OF THE INVENTION

In accordance with the present invention, the above-described shortcomings of conventional patient treatment methodologies are successfully overcome by a new and improved mechanism that is operative to quantify a patient's orthopaedic condition and any improvement of that condition, as well as the efficiency of the rehabilitation process employed to achieve a targeted patient improvement objective.

In particular, the present invention is directed to a medical condition quantification and dysfunction-reduction therapy evaluation process, that will enable the health care service provider to monitor the improvement, if any, of a patient's condition, as well as the efficiency of the rehabilitation process employed to achieve a patient improvement objective. To this end, based upon initial patient examination data, one or more sets of parameters associated with respective body regions, for which dysfunction-reducing therapy is to be carried out, are provided. Specific diagnoses per body region may be in the form of codes compatible with ICD-9 type codes of the International Classification of Diseases, 9th Revision, Clinical Modification provided by the World Health Organization, referenced above.

For each parameter code, a numerical data value is generated. The magnitude of the numerical data value is based upon the condition of the body region associated with the parameter. For orthopaedic applications, the body region may be one or more of cervical spine, thoracic spine, lumbar spine, shoulder, elbow, wrist, hip, knee, ankle, and foot. For a given movement condition, such as gross active range of motion of a body limb (wrist), a maximum data value may be associated with full movement of the limb (wrist) within its normal limits, a lesser range of values may be associated with limited painful movement, and a minimal value (e.g. zero) may be associated with a pathological condition in which movement is not possible.

The condition of the body region parameter will have been established in accordance with an examination of the patient, and is typically recorded in some form of patient history database, such as a preliminary examination report or auxiliary test result documentation. Once all of the parameters of a given body region have been assigned a numerical value, the data values are combined, for example, summed, to thereby quantify the overall condition or dysfunction of the body region. If the body region under consideration were fully functional, its quantified score would be a maximum value, for example, in the case of an orthopaedic condition, a value associated with full use and movement of the body region (e.g. wrist). For a dysfunctional condition for which therapy is to be carried out, however, the quantified total will be some lesser numerical value that is reduced from the maximal value as a result of the dysfunction. Ideally, therapy is intended to completely eliminate the dysfunction, so as to return the body region to its full capability (i.e., having an associated maximum numerical value).

Periodically, during the course of the patient therapy program, the physical condition of the body region being treated is re-examined. Based upon each re-examination, the numerical data value of each parameter is updated to reflect the current condition of body region, and the updated values are combined to thereby quantify the current dysfunction of the body region being treated.

By graphically recording both the original quantification of the dysfunction and the iteratively updated quantification results of the therapy session, the progress of the patient therapy program in reducing dysfunction of the body region can be readily tracked. Displaying the maximal numerical total associated with no dysfunction enables the health care service provider to not only monitor whether the therapy is reducing the dysfunction, but also how efficiently it is doing so, and whether complete recovery from the dysfunction is practically achievable.

If, over time, the therapy progress display reveals the dysfunction-reduction characteristic levelling off without reaching or becoming proximate the maximal quantification line, then it may be reasonably inferred that additional therapy sessions of the type currently being conducted may not be practically worthwhile, and a decision may be made to either change or terminate the treatment.

Quantifying, storing and displaying the dysfunction data not only allows the data to be compared with the maximal value data, representative of the maximum available combination of numerical data values representative of no dysfunction of the body region, but allows the data to be compared with other data, such as that representative of the measure of the progress of another patient therapy program. From this comparison, the success of the patient therapy program in reducing dysfunction can be determined in accordance with a prescribed relationship between the current patient's data and the other data representative of the measure of the progress of the other patient therapy program.

The measure of the progress of the patient therapy program may be derived in terms of cost of therapy and the reduction in dysfunction over the number of therapy sessions of the therapy program. Namely, body regions and specific ICD-9 diagnosis codes can be compared, overall therapist and facility effectiveness and efficiency averages can be calculated and compared allowing the health care providers, insurance industries, and patients an objective comparative statistic on effectiveness and efficiency, and costs as related to diagnostic code, body region, therapist, and facility.

BRIEF DESCRIPTION OF THE DRAWINGS

FIG. 4 lists six respective body regions: 1-cervical spine, upper quarter and thoracic spine; 2-shoulder; 3-elbow and wrist; 4-lumbar spine, lower quarter and hip; 5-knee; and 6-ankle and foot, together with their associated parameter;

FIG. 5 diagrammatically illustrates, for each parameter of FIGS. 3 and 4, a numerical data value, the magnitude of which is based upon the condition of the body region associated with the parameter;

DETAILED DESCRIPTION

Before describing in detail the new and improved quantitatively based (orthopaedic) therapy evaluation tool in accordance with the present invention, it should be observed that the present invention resides primarily in what is effectively a prescribed therapeutic data analysis mechanism, that is preferably implemented in software resident in a health care service provider's rehabilitation data management supervisory computer system, for enabling therapy personnel to monitor the progress of any orthopaedic patient to a dysfunction-reducing therapy program, and to make informed decisions whether and when to modify or terminate treatment.

Figure 1:
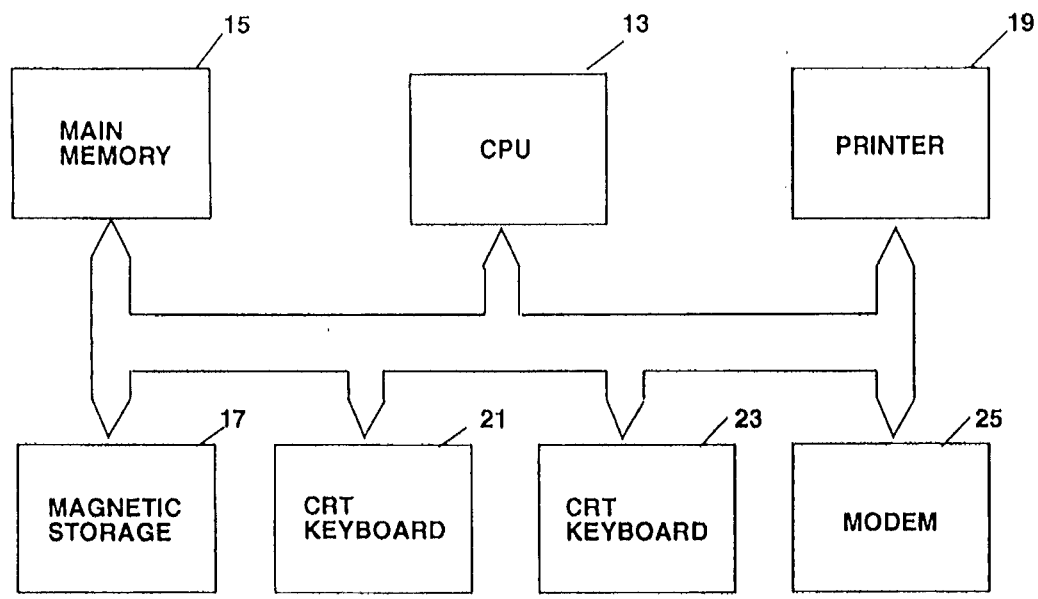
FIG. 1 diagrammatically illustrates a computer system, in which the quantitatively based mechanism of the present invention, for enabling therapy personnel to monitor the progress of any orthopaedic patient to a dysfunction-reducing therapy program may be employed.

Such a computer system is diagrammatically illustrated in FIG. 1 as comprising a common computer bus 11 to which various units that form the system are connected. These units include a central processing unit (CPU) 13, main (random access) memory 15, disc drive 17, printer 19, and a user interface 21 in the form of a keyboard 23 (and/or attendant mouse, not shown) and a video display terminal 23. To the extent desired one or more additional terminals may be provided. In addition, a modem 25 may be optionally provided to add external communication capability.

In FIGS. 2-6, the present invention has been illustrated in readily understandable block diagram format, which show only those specific details that are pertinent to the present invention, so as not to obscure the disclosure with details which will be readily apparent to those skilled in the art having the benefit of the description herein. Thus, the block diagram illustrations are primarily intended to illustrate the major components of a therapy progress quantifying system in a convenient functional grouping, whereby the present invention may be more readily understood.

Figure 2:
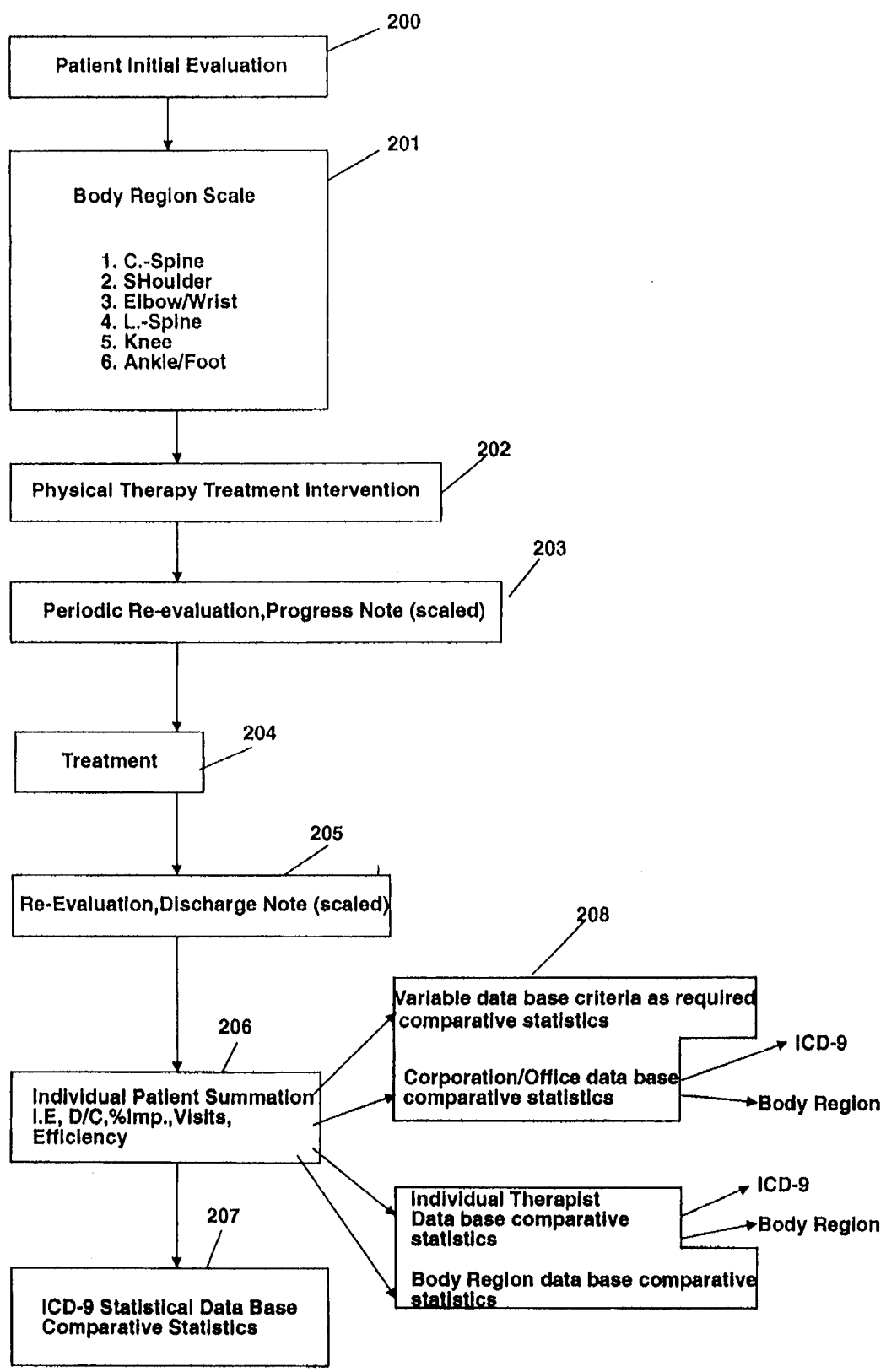
FIG. 2 diagrammatically illustrates the overall process flow of the respective steps of the orthopaedic condition quantification and dysfunction-reduction therapy evaluation process of the present invention.

The overall process flow of the respective steps of the orthopaedic condition quantification and dysfunction-reduction therapy evaluation process of the present invention, that enables the health care service provider to monitor the improvement, if any, of a patient's orthopaedic condition, as well as the efficiency of the rehabilitation process employed to achieve a patient improvement objective, is diagrammatically illustrated in FIG. 2.

As shown at step 201 therein, based upon initial patient examination data 200 supplied thereto, a set of parameters associated with one or more body regions, for which dysfunction-reducing therapy is to be carried out, is provided. As a non-limiting example, such parameters may be in the form of codes compatible with ICD-9 type codes of the International Classification of Diseases, 9th Revision, Clinical Modification provided by the World Health Organization, referenced above.

For the case of orthopaedic condition analysis and therapy, six respective body regions may be considered. As listed in step 201, and further characterized in FIGS. 3 and 4, such body regions comprise: 1-cervical spine, upper quarter and thoracic spine; 2-shoulder; 3-elbow and wrist; 4-lumbar spine, lower quarter and hip; 5-knee; and 6-ankle and foot.

Figure 3:
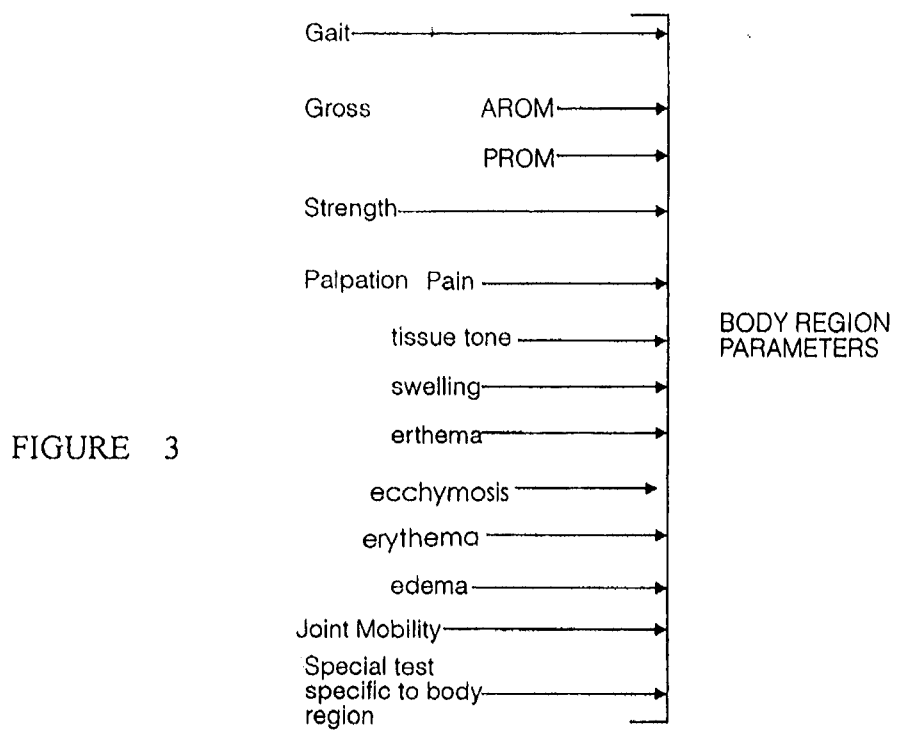
FIG. 3 shows a set of parameters associated with body regions including: gait, available range of motion (AROM), passive range of motion (PROM), strength, palpation pain, tissue tone swelling, erythema, ecchymosis, effusion, edema, joint mobility, and special tests that are specific to a body region.

As shown in FIG. 3, associated with each of these body regions is a set of parameters including: gait, available range of motion (AROM), passive range of motion (PROM), strength, palpation pain, tissue tone swelling, erythema, ecchymosis, effusion, edema, joint mobility, and special tests that are specific to a body region. The various special tests for the six respective body regions are set forth in detail in the column listings of FIG. 4.

As diagrammatically illustrated in FIG. 5, for each parameter, a numerical data value is generated. The magnitude of the numerical data value is based upon the condition of the body region associated with the parameter. In the illustrated examples of FIG. 5, for the parameter: gait, a maximum data value of 6 may be associated with full movement within normal limits (WNL), a protected, guarded or antalgic movement may be assigned a value of 4, the use of an assistive device (crutch) may be assigned a value of 2, and a minimal value (e.g. zero) may be associated with a pathological condition in which movement is not possible. Similarly, for gross active range of motion, a maximum data value of 12 may be associated with full movement within its normal limits, a lesser range of values 0–10 may be associated with limited painful movement. Where no determination is made as to what value should be assigned, the value may be deferred (D). The upper limit of the maximal value of each parameter is based upon an empirically defined range of integer values, that is sufficient to cover the entirety of variation of dysfunction for the parameter. Thus, the upper limit may vary among different parameters, since each parameter represents a unique pathological attribute.

As noted earlier, the condition of the body region will typically have been established at the time of initial examination of the patient, and may be recorded in some form of patient history database, such as a preliminary examination report or auxiliary test result documentation. Once all of the parameters have been assigned a numerical value, the data values are combined, for example, summed, to thereby quantify the overall dysfunction of the body region. If the body region under consideration were fully functional, the total quantified score of all its parameters would be a maximum available value associated with full use and movement of the body region. The total score for each respective body region is listed at the bottom of each respective column of FIG. 4.

Figure 6:
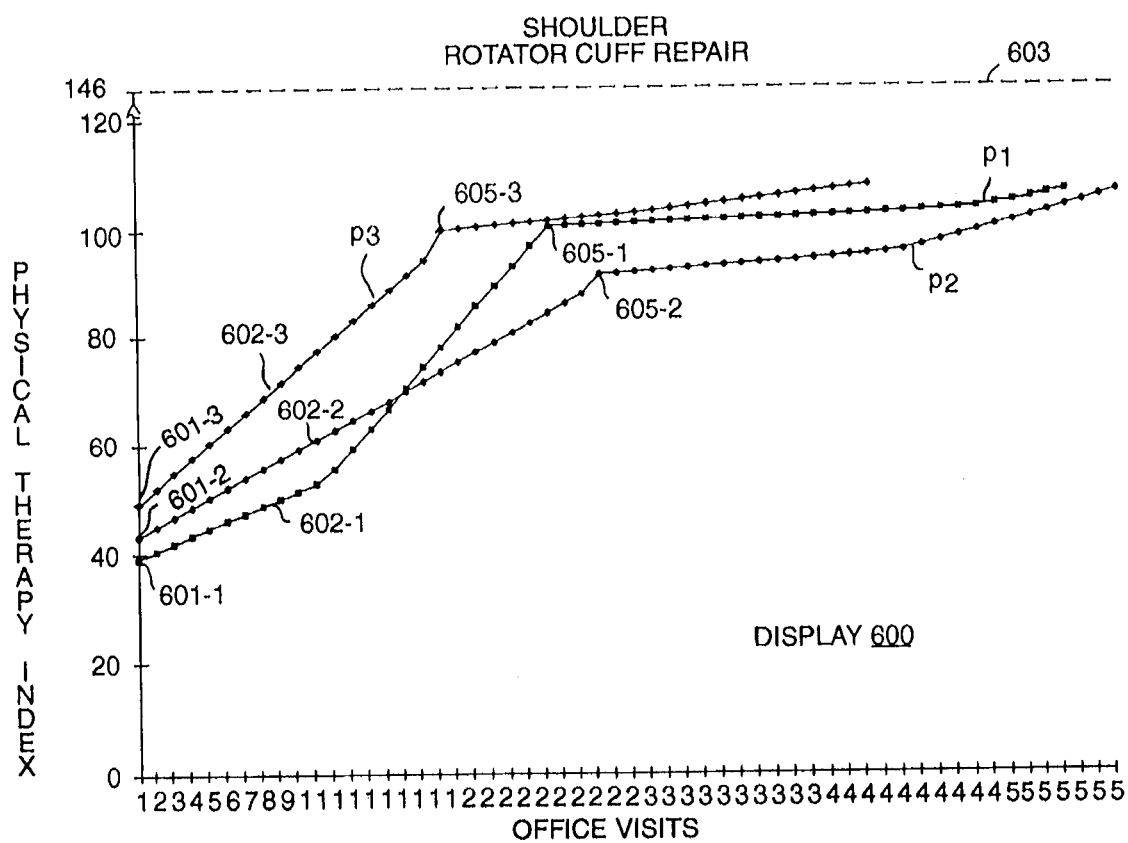
FIG. 6 is a graphical plot of the change in dysfunction-representative numerical total over successive therapy sessions.

For a dysfunctional condition, for which therapy is to be carried out, however, the quantified total will be some lesser numerical value. FIG. 6 shows the initial dysfunction representative totals associated with the shoulder, in particular, the rotator cuff, for three different patients P1, P2 and P3. At the beginning of treatment each patient has a respective total, graphically identified at the starting points 601-1, 601-2, 601-3 of treatment visit axis of a dysfunction improvement display 600. Successive therapy sessions are intended to cause an iterative reduction in and eventually a complete elimination of the dysfunction, as denoted by the improvement lines 602-1, 602-2 and 602-3, toward a maximal value line 603 associated with 100% rotator cuff and shoulder capability. (From FIG. 4, the shoulder has a maximal available score of 146.)

As successive therapy sessions are carried out during the course of the patient therapy program, as denoted by step 202 in FIG. 2, the physical condition of the body region being treated is re-examined, as shown at step 203. Based upon each re-examination, the numerical data value of each parameter is updated to reflect the current condition of the respective attribute associated with the parameter, and the updated values are combined to thereby quantify the current dysfunction of the body region being treated. In the case of the present example, these iteratively updated parameter values yield respective improvement characteristics 602-1, 602-2 and 602-3 in the graphical display of FIG. 6.

Namely, by graphically recording both the original quantification of the dysfunction (points 601-1, 601-2 and 601-3, in FIG. 6) and the iteratively updated quantification results of the therapy sessions, yielding the characteristic traces 602-1, 602-2 and 602-3 in the graphical plot of FIG. 6, the progress of the patient therapy program in reducing dysfunction of the body region is tracked. Displaying the maximal available numerical total line 603 (associated with no dysfunction) enables the health care service provider to not only monitor whether the therapy is reducing the dysfunction, but also how efficiently it is doing so, and whether total elimination of the dysfunction is practically achievable.

If, over time, through repeated treatments and re-evaluations, denoted by steps 204 and 205, respectively, of the process flow of FIG. 2, the therapy progress display reveals the dysfunction-reduction characteristic levelling off without reaching or becoming proximate the maximal quantification line, then it may be concluded that further therapy sessions of the type currently being conducted may not be practically worthwhile, and a decision may be made to either change the treatment, or terminate treatment and discharge the patient, as denoted by step 206.

For the three patients plotted in FIG. 6, it can be seen that each patient shows continuing improvement from the initial session up to respective knee points 605-1, 605-2 and 605-3, at which there is a substantial reduction in the slope of the characteristic. For patient P1, subsequent therapy sessions beyond session 24 reveal hardly any improvement. For patient P2, there is some, but not substantial, change beyond session 26. For patient P3, session 18 appears to be the session of diminishing returns. It will be appreciated that by using this graph, the therapist or other medical technician is able to make an informed decision as to the benefits of continued treatment at an early point in a sequence of treatments. For example, for patient P1, the levelling off of curve 602-1 past knee point 605-1 implies that further expenditures for treatment beyond twenty to thirty therapy sessions would not be cost effective.

It can be seen therefore that quantifying, storing and displaying the dysfunction data not only allows the data to be compared with the maximal value data line 603, representative of the maximum available combination of numerical data values representative of no dysfunction of the body region, but allows the data to be compared with other data, such as that representative of the measure of the progress of another patient therapy program, as shown at steps 207 and 208 in the process flow of FIG. 2. From such comparison, the success of patient therapy in reducing dysfunction can be determined in accordance with a prescribed relationship between the current patient's data and the other data representative of the measure of the progress of the other patient therapy program.

The measure of the progress of the patient therapy program may be derived in terms of cost of therapy and the reduction in dysfunction over the number of therapy sessions of the therapy program. Namely, as shown at steps 208 and 209, body regions and specific ICD-9 diagnosis codes can be compared, overall therapist and facility effectiveness and efficiency averages can be calculated and compared allowing the health care providers, insurance industries, and patients an objective comparative statistic on effectiveness and efficiency, and costs as related to diagnostic code, body region, therapist, and facility.

As will be appreciated from the foregoing description, the present invention provides a medical condition quantification and dysfunction-reduction therapy evaluation process, that will enable the health care service provider to monitor the improvement, if any, of a patient's condition, as well as the efficiency of the rehabilitation process employed to achieve a patient improvement objective. The information employed in the method according to the present invention may be based upon clinician documented evaluative procedures performed during initial evaluation, daily treatment, re-evaluation, and at patient discharge. It is also to be noted that technique being described here is not limited to a particular version of the ICD diagnosis and procedure classification system, but rather will use whatever system is current at the time.

The ICD-9 coding system was designed for the classification of morbidity and mortality information for statistical purposes and for the ordering of hospital records by disease and operations of data storage and retrieval. The ICD-9 codes are initially divided into disease and procedure sections. These sections are further divided into subsections which encompass anywhere from 1–999 three digit disease or 1–99 two digit procedure code categories. Within the three digit code categories, there can be an additional 1 or 2 decimal digit to divide the codes into subcategories which further define the disease manifestations and/or diagnostic procedures. There are approximately 15,000 ICD-9 codes. Only a portion of these are relevant for rehabilitation and orthopaedic dysfunction.

While I have shown and described an embodiment in accordance with the present invention, it is to be understood that the same is not limited thereto but is susceptible to numerous changes and modifications as known to a person skilled in the art, and I therefore do not wish to be limited to the details shown and described herein but intend to cover all such changes and modifications as are obvious to one of ordinary skill in the art.

What is claimed:

1. A method of evaluating progress of a patient therapy program, through which dysfunction of a body region of said patient may be reduced, comprising the steps of:

(a) providing a plurality of of respectively different parameters representative of respectively different physical attributes of said body region for which dysfunction-reducing therapy is to be carried out;

(b) for each respectively different parameter of said plurality, generating a respective numerical data value that represents a condition of a respectively different physical attribute of said body region associated with said each respectively different parameter, and combining numerical data values of said respectively different parameters, so as to quantify said dysfunction of said body region;

(c) conducting a patient therapy program for reducing said dysfunction of said body region;

(d) during said patient therapy program conducted in step (c), re-evaluating a physical condition of said body region, and for each respectively different parameter of said plurality, generating an updated numerical data value that represents a current condition of said respectively different attribute of said body region associated with said each respectively different parameter, and combining updated numerical data values, so as to quantify a current dysfunction of said body region; and (e) deriving a measure of progress of said patient therapy program in reducing dysfunction of said body region in accordance with differences in dysfunction of said body region as quantified in steps (d) and (b).

2. A method according to claim 1, wherein step (d) comprises, during said patient therapy program conducted in step (c), successively re-evaluating said dysfunction of said body region and, for each successive re-evaluation, generating an updated numerical data value for each respectively different parameter of said plurality, which updated numerical value represents a current condition of said respectively different attribute of said body region associated with said each respectively different parameter, and combining updated numerical values, so as to quantify said current dysfunction of said body region, and wherein step (e) comprises deriving a measure of the progress of said patient therapy program in reducing dysfunction of said body region in accordance with changes in quantified dysfunction of said body region.

3. A method according to claim 2, wherein step (a) comprises providing a plurality of respectively different orthopaedic parameters associated with respectively different orthopaedic attributes of said body region, for which orthopaedic dysfunction-reducing therapy is to be carried out, and wherein step (b) comprises, for each respectively different orthopaedic parameter of said plurality, generating a numerical data value that represents a condition of said respectively different orthopaedic attribute, and combining numerical data values of respectively different parameters of said plurality, so as to quantify an orthopaedic condition of said body region.

4. A method according to claim 3, wherein step (d) comprises, during the patient therapy program conducted in step (c), successively re-evaluating said orthopaedic condition of said body region and, for each successive re-evaluation, generating an updated numerical data value for each respectively different orthopaedic parameter of said plurality, which updated numerical data value represents a on current orthopaedic condition of a respectively different orthopaedic attribute associated with said each respectively different orthopaedic parameter, and combining the updated numerical values, so as to quantify a current orthopaedic dysfunction of said body region, and wherein step (e) comprises deriving a measure of said progress of said patient therapy program in reducing said orthopaedic dysfunction of said body region in accordance with changes in quantified orthopaedic dysfunction of said body region.

5. A method according to claim 2, further including the step (f) of modifying said patient therapy program in response to a prescribed change in said quantified dysfunction of said body region.

6. A method according to claim 2, further including the step (f) of terminating said patient therapy program in response to a prescribed change in said quantified dysfunction of said body region.

7. A method according to claim 2, further including the step (f) of storing data representative of the measure of the progress of said patient therapy program derived in step (e).

8. A method according to claim 7, further including the step (g) of comparing the data stored in step (f) with other data, said other data being representative of a maximum available combination of numerical data values associated with said respectively different parameters of said plurality representative of no dysfunction of said body region, to derive a measure of the progress of said patient therapy program, and selectively modifying the patient therapy program carried out in step (c), in accordance with a prescribed relationship between the data stored in step (f) and said other data.

9. A method according to claim 7, further including the step (g) of comparing the data stored in step (f) with other data representative of the measure of the progress of another patient therapy program, and selectively modifying the patient therapy program carried out in step (c), in accordance with a prescribed relationship between the data stored in step (f) and said other data representative of the measure of the progress of said another patient therapy program.

10. A method according to claim 7, further including the step of (g) comparing the data stored in step (f) with other data representative of the measure of progress of another patient therapy program, and generating an output representative of success of the patient therapy program carried out in step (c) in reducing said dysfunction, in accordance with a prescribed relationship between the data stored in step (f) and said other data representative of the measure of the progress of said another patient therapy program.

11. A method according to claim 7, wherein said measure of the progress of said patient therapy program is derived in terms of cost of therapy and reduction in dysfunction over a number of therapy sessions of said patient therapy program.

12. A method according to claim 1, wherein the numerical data value generated in step (b) represents where, within a range of possible conditions of said respectively different physical attribute of said body region, the condition of said respectively different physical attribute of said body region occurs.

13. A method according to claim 12, wherein said range of possible conditions of said respectively different physical attribute of said body region is defined in accordance with respectively different degrees of orthopaedic capability of said body region.

14. A method according to claim 1, wherein said respectively different parameters associated with said respectively different attributes of said body region comprise codes compatible with ICD-9 type codes of the International Classification of Diseases, 9th Revision, Clinical Modification provided by the World Health Organization.

15. A method according to claim 1, wherein step (a) comprises providing said plurality of respectively different parameters associated with respectively different physical attributes of said body region for which dysfunction-reducing therapy is to be carried out, in accordance with physical therapy documentation generated as a result of an evaluation of a physical condition of said patient.

16. A method according to claim 1, wherein said body region is one selected from the group consisting of cervical spine, thoracic spine, lumbar spine, shoulder, elbow, wrist, hip, knee, ankle, and foot.

17. A method of evaluating progress of a patient therapy program, through which dysfunction of one or more body regions of said patient may be reduced, comprising the steps of:

(a) evaluating a physical condition of a patient to identify one or more body regions for which dysfunction-corrective therapy may be required and, for each identified body region, establishing a plurality of respectively different parameters representative of respectively different physical attributes of said each identified body region;

(b) for each respectively different parameter of a respective plurality established in step (a), generating a numerical data value that represents a physical condition of a respective body region, and combining the numerical values of said respective plurality, so as to quantify said physical condition of said respective body region;

(c) for each respective body region identified in step (a), conducting a patient therapy program for reducing dysfunction thereof;

(d) during the patient therapy program conducted in step (c), re-evaluating the physical condition of each respective identified body region for which dysfunction-corrective therapy has been carried out, and for each respectively different parameter of a respective plurality, generating an updated numerical data value that represents a current physical condition of said each respective identified body region, and combining updated numerical values of said respective plurality, so as to quantify the current condition of said each respective identified body region; and (e) deriving a measure of the progress of said patient therapy program in accordance with changes in quantified condition of said each respective identified body region.

18. A method according to claim 17, wherein step (a) comprises identifying one or more body regions for which orthopaedic dysfunction-corrective therapy of said patient may be required and, for each identified body region, establishing a respective plurality of respectively different orthopaedic parameters associated with respectively different orthopaedic attributes thereof.

19. A method according to claim 18, wherein step (b) comprises, for each respectively different orthopaedic parameter of a respective plurality established in step (a), generating a numerical data value that represents a condition of an associated orthopaedic attribute, and combining numerical values of said respective plurality, so as to quantify an orthopaedic condition of said each respective identified body region.

20. A method according to claim 19, wherein step (d) comprises re-evaluating said orthopaedic condition of said each respective identified body region for which orthopaedic dysfunction-corrective therapy has been carried out, and for each respectively different orthopaedic parameter of a respective plurality, generating an updated numerical data value that represents a current orthopaedic condition of a respectively associated orthopaedic attribute, and combining updated numerical values of said respective plurality, so as to quantify a current orthopaedic condition of said each respective identified body region.

21. A method according to claim 17, wherein the numerical data value generated in step (b) represents where, within a range of possible physical conditions of a respective body region, the condition of said respective body region occurs.

22. A method according to claim 21, wherein said range of possible conditions of said respective body region is defined in accordance with respectively different degrees of orthopaedic capability of said respective body region.

23. A method according to claim 17, further including the step (f) of modifying said patient therapy program in response to a prescribed change in a quantified condition of said each respective identified body region.

24. A method according to claim 17, further including the step (f) of terminating said patient therapy program in response to a prescribed change in a quantified condition of said each respective identified body region.

25. A method according to claim 17, further including the step (f) of storing data representative of the measure of the progress of said patient therapy program derived in step (e).

26. A method according to claim 25, further including the step (g) of comparing the data stored in step (f) with other data, said other data being representative of a maximum available combination of numerical data values associated with the respectively different parameters of said respective plurality representative of no dysfunction of said respective body region, to derive a measure of the progress of said patient therapy program, and selectively modifying the patient therapy program carried out in step (c), in accordance with a prescribed relationship between the data stored in step (f) and said other data.

27. A method according to claim 25, further including the step (g) of comparing the data stored in step (f) with other data representative of a measure of progress of another patient therapy program, and selectively modifying the patient therapy program carried out in step (c), in accordance with a prescribed relationship between the data stored in step (f) and said other data representative of the measure of the progress of said another patient therapy program.

28. A method according to claim 25, further including the step of (g) comparing the data stored in step (f) with other data representative of a measure of progress of another patient therapy program, and generating an output representative of the success of the patient therapy program carried out in step (c) in reducing said dysfunction, in accordance with a prescribed relationship between the data stored in step (f) and said other data representative of the measure of the progress of said another patient therapy program.

29. A method according to claim 25, wherein said measure of the progress of said patient therapy program is derived in terms of cost of therapy and a reduction in dysfunction over a number of therapy sessions of said therapy program.

30. A method according to claim 17, wherein said respectively different parameters representative of respectively different physical attributes of a respective identified body region comprise codes compatible with ICD-9 type codes of the International Classification of Diseases, 9th Revision, Clinical Modification provided by the World Health Organization.

31. A method according to claim 17, wherein step (a) comprises establishing a plurality of respectively different parameters representative of respectively different physical attributes of a body region, for which dysfunction-reducing therapy is to be carried out, in accordance with physical therapy documentation generated as a result of an evaluation of a physical condition of said patient.

32. A method according to claim 17, wherein a respective body region is one selected from the group consisting of cervical spine, thoracic spine, lumber spine, shoulder, elbow, wrist, hip, knee, ankle, and foot.

* * * * *